(12) United States Patent
Zahalsky

(10) Patent No.: US 11,786,270 B2
(45) Date of Patent: Oct. 17, 2023

(54) PENILE INJECTION GUIDE AND COMPRESSION DEVICE

(71) Applicant: Michael P. Zahalsky, Parkland, FL (US)

(72) Inventor: Michael P. Zahalsky, Parkland, FL (US)

(*) Notice: Subject to any disclaimer, the term of this patent is extended or adjusted under 35 U.S.C. 154(b) by 701 days.

(21) Appl. No.: 16/998,176

(22) Filed: Aug. 20, 2020

(65) Prior Publication Data

US 2020/0390466 A1    Dec. 17, 2020

Related U.S. Application Data

(62) Division of application No. 15/968,378, filed on May 1, 2018, now Pat. No. 10,779,854.

(51) Int. Cl.

| A61B 17/34 | (2006.01) |
| A61M 5/32 | (2006.01) |
| A61B 90/92 | (2016.01) |
| A61B 17/00 | (2006.01) |

(52) U.S. Cl.
CPC .......... *A61B 17/3403* (2013.01); *A61B 90/92* (2016.02); *A61M 5/3287* (2013.01); *A61B 2017/00862* (2013.01); *A61B 2017/3407* (2013.01); *A61B 2017/3411* (2013.01); *A61M 2210/167* (2013.01)

(58) Field of Classification Search
CPC ........ A61B 17/3403; A61B 2017/3411; A61B 2017/3407; A61B 2017/00862; A61B 90/11; A61B 90/92; A61M 5/3287; A61M 5/427; A61M 5/46; A61M 2210/167; A61M 35/003; A61M 2205/584; A61M 2205/6081; A61F 2005/411; A61F 5/41; A61F 6/04
See application file for complete search history.

(56) References Cited

U.S. PATENT DOCUMENTS 4,846,197 A * 7/1989 Benjamin ................. A61F 6/04
                                                    604/353
5,513,652 A    5/1996 Schwartz
5,823,191 A * 10/1998 Cho .......................... A61F 6/04
                                                    128/918

(Continued)

OTHER PUBLICATIONS

Memorial Sloan Kettering Cancer Center, "Penile Injection Therapy", Dec. 7, 2017 (Year: 2017).*

(Continued)

*Primary Examiner* — Emily L Schmidt
*Assistant Examiner* — Alexandra Lalonde
(74) *Attorney, Agent, or Firm* — David L. King

(57) ABSTRACT

A conformable guide for directing penile injections has an elastomeric or conformable tube having an open end distally for passing over a glans and a shaft of a penis toward a root of the penis on placement. The conformable guide can have an annulus shaped spirally wrapped portion of the elastomeric tube at the distal end configured to unwrap on placement toward the root. The elastomeric tube has one or more observable injection site locations marked or otherwise indicated on the elastomeric tube when positioned onto the shaft of the penis. The conformable guide is made of a stretchable synthetic polymer.

9 Claims, 5 Drawing Sheets

(56) References Cited

U.S. PATENT DOCUMENTS

| | | | | |
|---|---|---|---|---|
| 5,857,466 | A | * | 1/1999 | Sadlo ........................ A61F 6/04 |
| | | | | 128/918 |
| 2012/0035410 | A1 | * | 2/2012 | Borgos ...................... A61F 5/41 |
| | | | | 600/15 |
| 2015/0141961 | A1 | * | 5/2015 | Terlecki .............. A61M 5/3287 |
| | | | | 604/116 |
| 2017/0182242 | A1 | | 6/2017 | Galitz et al. |
| 2019/0021897 | A1 | * | 1/2019 | Lange, IV ................ A61F 5/41 |

OTHER PUBLICATIONS

Penile Injection Therapy, Dec. 8, 2017, Memorial Sloan Kettering Cancer Center (Year: 2017).

Kendirci M et al. Transplantation of non-hematopoietic adult bone marrow stem/progenitor cells isolated by the p75 nerve growth factor receptor into the penis rescues ED in a rat model of cavernous nerve injury. J. Urol. 2010; 184(4): 1560-1566.

Woo J C et al. Transplantation of muscle-derived stem cells into the corpus cavernosum restores erectile function in a rat model of cavernous nerve injury. Korean J. Urol. 2011; 52: 359-363.

Hauck E W et al. A critical analysis of nonsurgical treatment of Peyronie's disease. European Urology 2006, 49(6): 987-97.

* cited by examiner

PENILE INJECTION GUIDE AND COMPRESSION DEVICE

RELATED APPLICATIONS

The present invention is a division of U.S. application Ser. No. 15/968,378; now U.S. Pat. No. 10,779,854; filed on May 1, 2018 entitled "Penile Injection Guide And Compression Device".

TECHNICAL FIELD

The present invention relates to an injection guide for injecting medications into a penis. The medication can include biologic materials and even viable stem cells.

BACKGROUND OF THE INVENTION

One area of interest is that of penile defects, such as erectile dysfunction (ED) and Peyronie's disease. At least some forms of ED trace their etiology to vascular deficits in the penile tissue. Pharmaceutical compositions for treating ED do exist; however, a need exists for more advanced treatments that may require use of medicaments. At least one group has reported success in the use of stem cells derived from bone marrow to reverse ED in an animal model. Kendirci M et al. Transplantation of non-hematopoietic adult bone marrow stem/progenitor cells isolated by the p75 nerve growth factor receptor into the penis rescues ED in a rat model of cavernous nerve injury. J. Urol. 2010; 184(4): 1560-1566. Another group has seen success in using muscle-derived stem cells in a rat model of ED. Woo J C et al. Transplantation of muscle-derived stem cells into the corpus cavernosum restores erectile function in a rat model of cavernous nerve injury. Korean J. Urol. 2011; 52: 359-363.

Peyronie's disease is an ailment involving the growth of fibrous plaques in the soft tissue of the penis. These plaques grow in the tunica albuginea, a region of connective tissue that is part of the more general connective tissue of Buck's fascia. The tunica albuginea is an area surrounding the corpora cavernosa. The disease results in pain, ED, and alteration of penis shape, and may be caused by disorganized collagen fibers. Treatments for the disease currently include administration of corticosteroids to the plaques, radiation therapy, and vitamin E Pharmaceuticals for treatment exist; however, the use of medicaments is considered controversial in the art, and these compounds have not met with sustained success. Hauck E W et al. A critical analysis of nonsurgical treatment of Peyronie's disease. European Urology 2006; 49(6): 987-97.

To take full advantage of these opportunities, improved capabilities are needed.

In order to correct penile defects such as Peyronie's disease or erectile dysfunction, it is known to inject medications into the tissue of the patient's penis. This procedure can typically be done in a doctor's office under supervision of a trained professional. It is important when injecting the penis that the medications be delivered to the locations in need of treatment while avoiding areas that could cause damage.

Many of the new medications used during these procedures can include biological products such as stem cells or other organic material that needs to be strategically placed along the shaft of the penis. To assist the doctor that the injections are properly positioned and the correct dosage is given in each location, it is desirable to provide a means of assistance to help assist the doctor delivering the proper dosage to the proper location on a very consistent and reliable basis.

In some cases, it may be possible for the patient to self-inject himself with medications to assist in the repair and recovery process. The self-injections will most likely occur at the patient's home without supervision of a trained professional. This is very similar to diabetic patients who routinely inject themselves with insulin. In such cases, it is important that the medications be delivered in the proper dosage at the proper location. To achieve this, a guide system has been created according to the present invention described here in to assist the procedure.

SUMMARY OF THE INVENTION

A conformable guide for directing penile injections has an elastomeric or conformable tube having an open end distally for passing over a glans and a shaft of a penis toward a root of said penis on placement. The conformable guide can have an annulus shaped spirally wrapped portion of the elastomeric tube at the distal end configured to unwrap on placement toward said root. The elastomeric tube has one or more observable injection site locations marked or otherwise indicated on the elastomeric tube when positioned onto the shaft of the penis. The elastomeric tube has a top side placement indication at a 12 o'clock or 0 degree orientation at said top side and the injection site locations are at 10 o'clock and 2 o'clock locations. Preferable, the elastomeric tube has a no injection marker indication or stripe at a location of about 6 O'clock or 180 degrees spanning a width of 5 to 7 o'clock or 150 to 210 degrees, or 4 to 8 o'clock or 120 to 240 degrees. The conformable guide is made of an elastomeric material, preferably a latex or synthetic polymer material sized to stretch when placed over an erect shaft to provide a compressive force around the tissue of the shaft being injected.

The annulus shaped portion at the root holds the tube securely to said root of said shaft. The guide allows for a method of treating a patient's penis comprises the steps of: placing a conformable guide onto the penis; aligning a top side of said guide with a top side of the penis; passing the guide over the glans onto the shaft and moving a distal portion of said guide onto a root of said shaft, wherein the conformable guide has one or more injection site locations marked or otherwise indicated along the conformable guide; and injecting medications through the one or more said injection site locations into said penis to treat the male organ. The conformable guide has an annulus shape wrapped portion at a distal end of an elastomeric tube forming the conformable guide further comprises unwrapping the annulus shaped portion conformable guide toward the root to secure said guide to the penis. Preferably, the patient is provided a treatment or dosage of material to induce an erection prior to placement or after placement of the conformable guide.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines or type of stem cell, constructs, additives, and reagents described herein. It is also to be understood that the terminology used herein is for the purpose of describing particular embodiments only, and is not intended to limit the scope of the present invention which will be limited only by the appended claims.

The term "stem cell" refers to any multipotent or pluripotent cell, traditional stem cells, progenitor cells, preprogenitor cells, and reserve cells. The term is used interchangeably with and may mean progenitor cell. The stem cell may be derived from an adult organism or from a cell line, or from an embryonic organism. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, and the like. Descriptions of stem cells, including method for isolating and culturing them, may be found in, among other places, Embryonic Stem Cells, Methods and Protocols, Turksen ed., Humana Press, 2002.

The term "adult" as used herein refers to any non-embryonic organism. For example the term "adult adipose-derived regenerative cell," refers to an adipose-derived regenerative cell, other than that obtained from an embryo.

The term "embryo" as used herein refers to any multicellular diploid eukaryote during development, until birth or hatching. The term "embryonic stem cell" refers to a pluripotent cell derived from the inner cell mass of a blastocyst.

The term "mesenchymal stem cell" refers to any multipotent stromal cell derived from, for example and without limitation, umbilical cord blood, adipose tissue, muscle, corneal stroma, and dental pulp that can differentiate into cells such as, including but not limited to, osteoblasts, chondrocytes, and adipocytes.

The term "adipose-derived regenerative cell" (ADRC) is used interchangeably with adipose stem cells (ASC) herein and refers to adult cells that originate from adipose tissue. ADRC are a heterologous population of cells comprising at least one of the following population of cells; adult stem cells, vascular endothelial cells, vascular smooth muscle cells, endothelial cells, mesenchymal stem cells, fibroblasts, pericytes and additional other cell types.

In some embodiments, ADRC refers to a substantially pure population of adipose-derived stem cells. ADRC can be easily harvested from adipose tissue and are substantially free of adipocytes and red blood cells and clonal populations of connective tissue stem cells. The stromal vascular fraction cells are substantially devoid of extracellular matrix material from adipose tissue. ADRC may also be referred to as adipose-derived stem/stromal cells (ASCs), adipose-derived adult stem (ADAS) cells, adipose-derived adult stromal cells, adipose-derived stromal cells, adipose stromal cells, adipose mesenchymal cells, adipose-derived mesenchymal stem cells, lipoblasts, pericytes, preadipocytes, and processed lipoaspirate cells.

The term "adipose" as used herein refers to any fat tissue from a subject. The terms "adipose" and "adipose tissue" are used interchangeably herein. The adipose tissue may be brown fat, white fat or yellow fat or white adipose tissue, derived from subcutaneous, omental/visceral, mammary, gonadal, or other adipose tissue site. The adipose tissue has adipocytes and stroma. Adipose tissue is found throughout the body of an animal. For example, in mammals, adipose tissue is present in the omentum, bone marrow, subcutaneous space, and surrounding most organs. Such cells may comprise a primary cell culture or an immortalized cell line. The adipose tissue may be from any organism having fat tissue.

Preferably, the adipose tissue is human; most preferably, the adipose tissue is derived from the individual in need of treatment for a penile defect. A convenient source of adipose tissue is from liposuction surgery, however, the source of adipose tissue or the method of isolation of adipose tissue is not critical to the invention, and acquisition of adipose tissue by any means may adequately provide tissue and stem cells for the present invention.

The term "tissue" as used herein is a broad term that is applied to any group of cells that perform specific functions, and includes in some instances whole organs and/or part of organs. A tissue need not form a layer, and thus encompasses a wide range of tissue, including adipose tissue derived from any source in an organism. Preferably, the tissue is derived from a mammal Most preferably, the tissue is derived from the individual in need of treatment for a penile defect.

The term "implant" as used herein refers to any method for transferring a population of cells or cell mass into a subject, including by surgical implantation (incision into the tissue of interest and deposition therein) and injection by a syringe, needle, cannula, or the like of any suitable gauge. An implant as used herein can comprise genetically modified cells, as well as cells differentiated from other cells, such as stem cells, progenitors, and the like, as well as adipose cells or tissue.

The term "corpus cavernosum" of the penis refers to one of a pair of sponge-like regions of erectile tissue which contain most of the blood in the penis during penile erection. Generally, the two corpus cavernosum and a corpus spongiosum are three expandable erectile tissues along the length of the penis which fill with blood during erection. The term "corpus" is used interchangeably herein with corporal, corporeal and corporic, which are terms used to describe tissues which are derived from the corpora cavernosum or which can be developed, differentiated, or altered by natural or artificial means into corpora cavernosum tissue. The term "cavernosum" is used interchangeably herein as cavernae, corporum, cavernosum, or cavernosorum penis, and refers to the caverns of corpora cavernosa (or one of the two corpus cavernosum) of the penis or the dilatable spaces within the corpus cavernosum of the penis, which fill with blood and become distended with erection.

The term "tunica albuginea" refers to the fibrous tissue covering, or enveloping, the corpora cavernosa of the penis. This tissue consists of elastin and collagen. The term "Bucks fascia" refers to the layer of fascia covering the penis, including the tunica albuginea.

The terms "subject" and "individual" are used interchangeably herein, and refer to an animal, for example a human, from whom a adipose tissue and stem cells, for example ADRC can be harvested, or a subject into whom tissue can be transplanted for treatment, for example treatment for penile defects, using the compositions and methods described herein. For treatment of conditions or disease states which are specific for a specific animal such as a human subject, the term "subject" refers to that specific animal. In some embodiments, the subject is a human subject. It is possible in embodiments of this invention that recipient subjects are of a different mammalian subject than the donor subject.

BRIEF DESCRIPTION OF THE DRAWINGS

The invention will be described by way of example and with reference to the accompanying drawings in which.

DETAILED DESCRIPTION OF THE INVENTION

Figure 1:
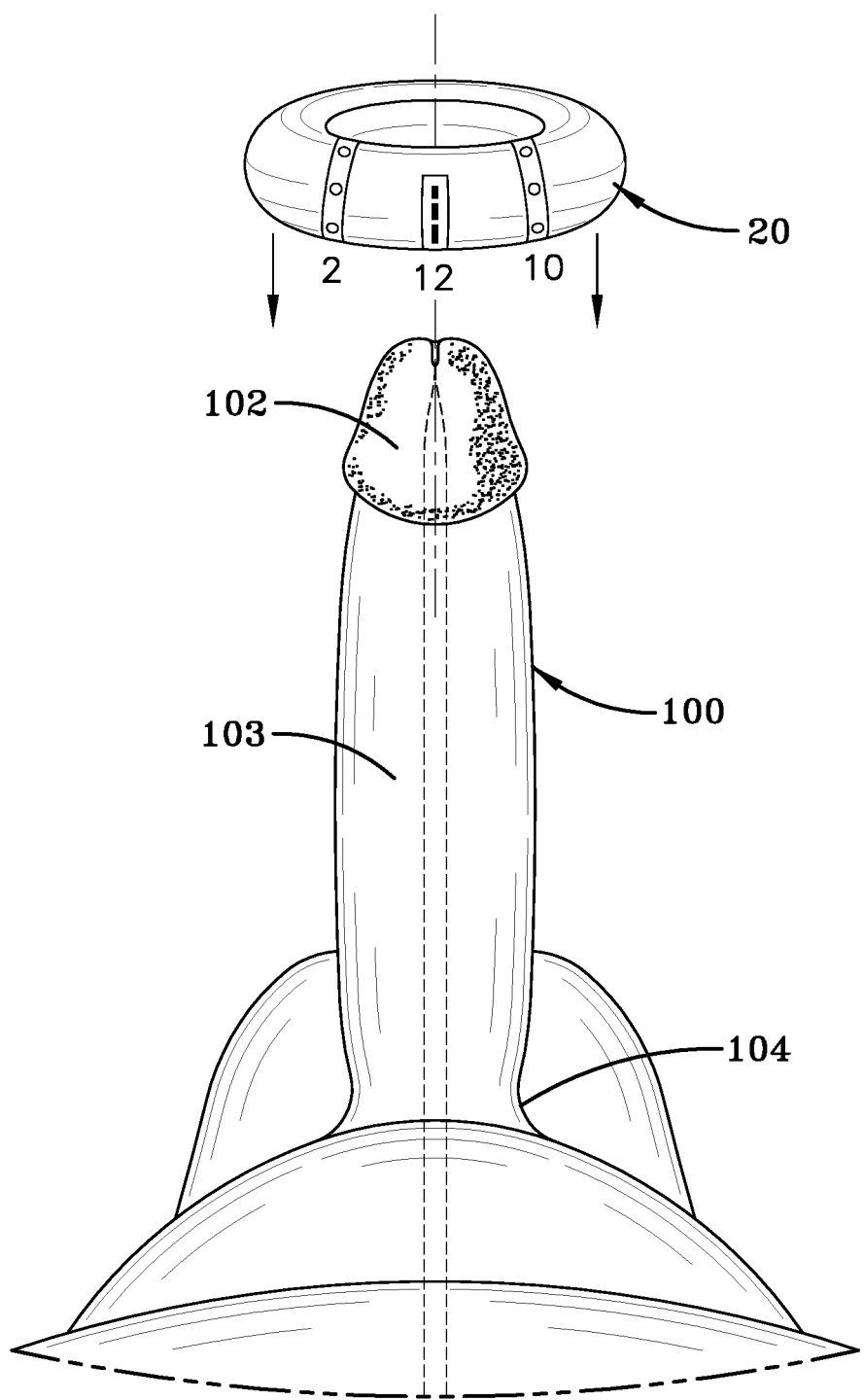
FIG. 1 is a perspective view of the conformable guide above a penis.

With reference to FIGS. 1 through 5, a conformable device is shown. The conformable device being a conformable guide 20 which used to facilitate delivering injections to a penis 100. As illustrated in FIG. 1, the conformable guide 20 is shown as an annular ring or donut shaped device above the glans 102 of the penis 100. The directional arrows shown that the conformable guide 20 is moved towards the erect penis in FIG. 1. Optionally, the donut shaped device can be slid down the shaft of the penis and the spiral wrap can be unwound from the root 104 or base of the shaft 103 toward the glans 102 near the tip of the penis 101.

Figure 2:
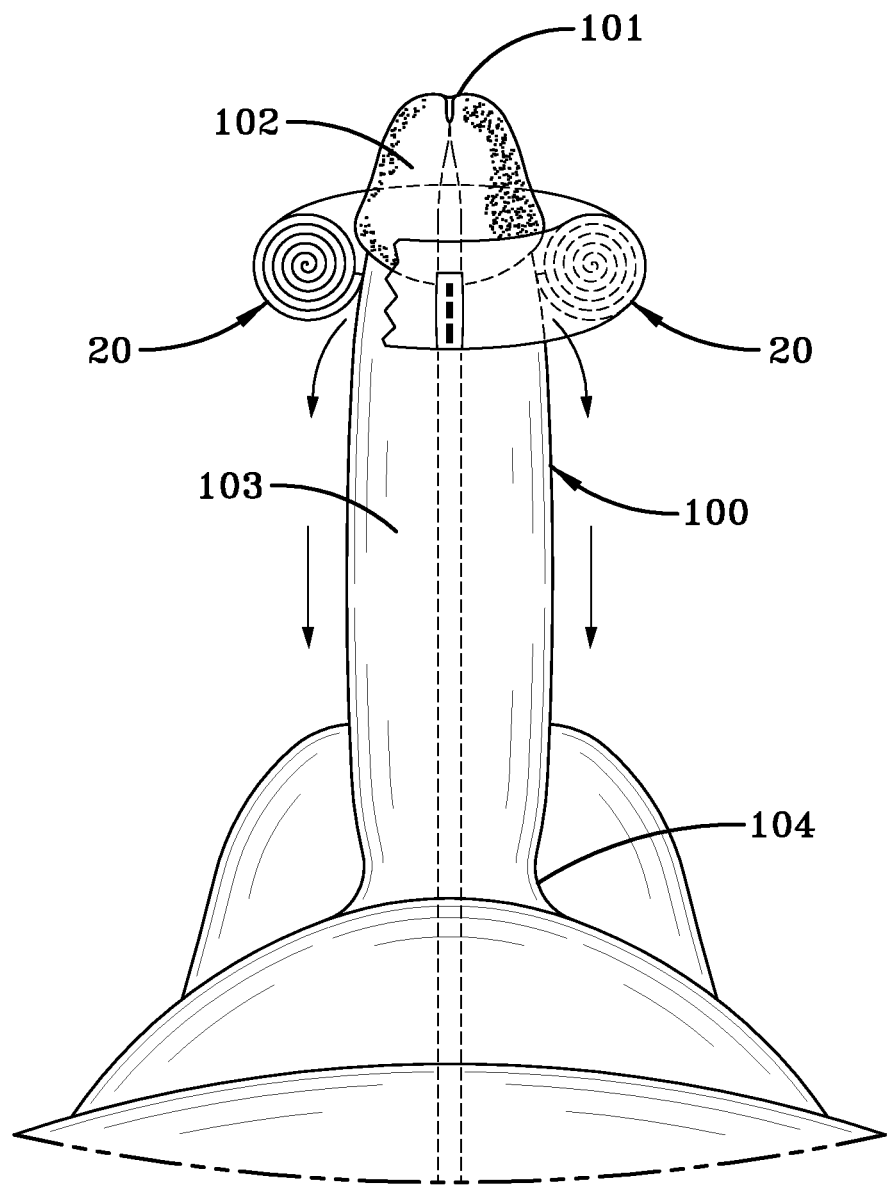
FIG. 2 is a partial cross section of the conformable guide shown placed over and past the glans of the penis onto the shaft.

As shown in FIG. 2, a partial cross-sectional view of the annular conformable guide 20 is illustrated. The annular conformable guide 20, as illustrated, is spirally wound to form the donut or annular shaped ring which is passed over the glans 102, as illustrated in FIG. 2, just past the glans 102 and is unwrapped along the shaft 103 of the penis towards the base or root 104 or alternatively positioned as described above.

Figure 3:
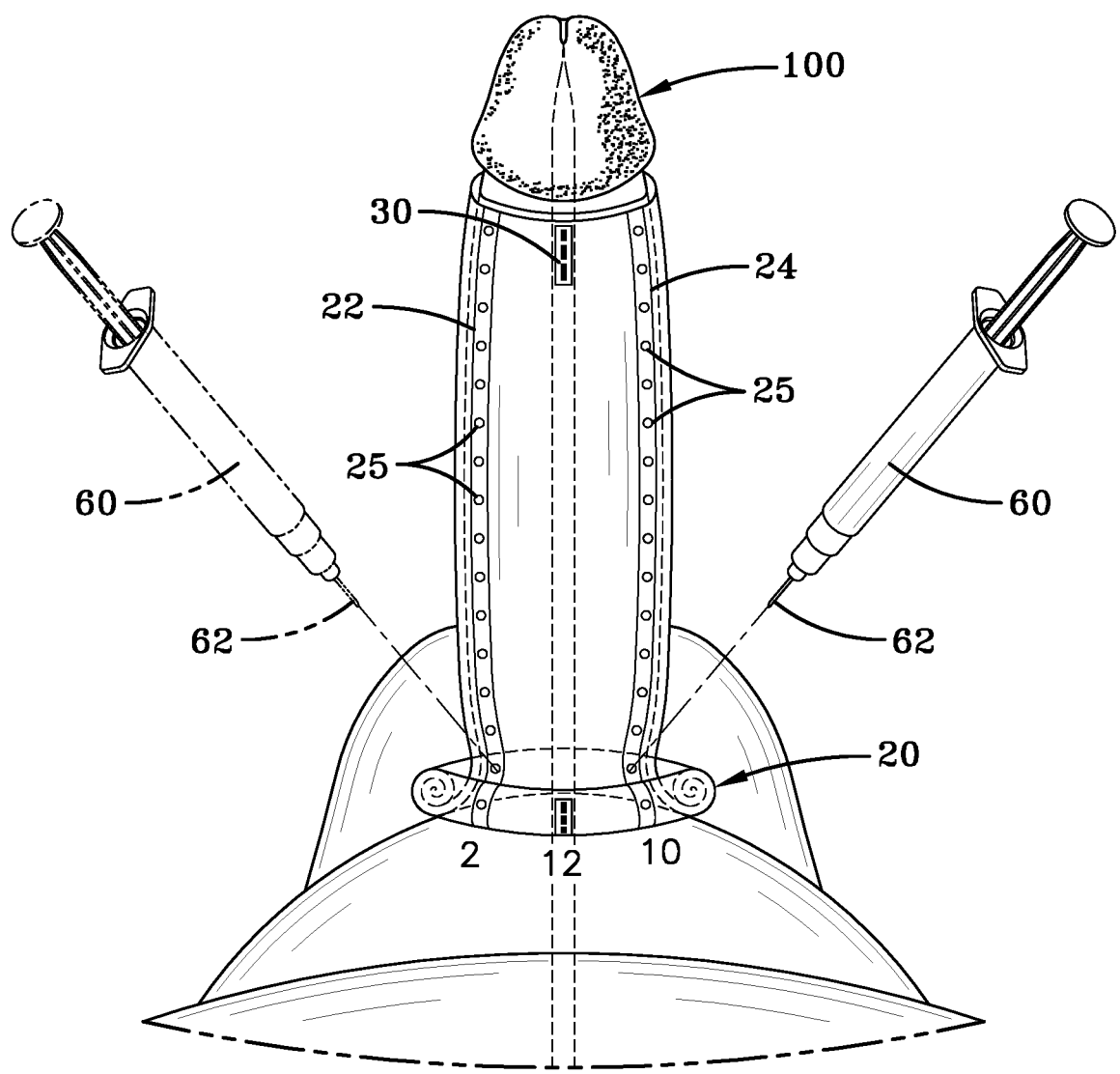
FIG. 3 is a view of the guide when unwrapped and placed onto the shaft.
Figure 4:
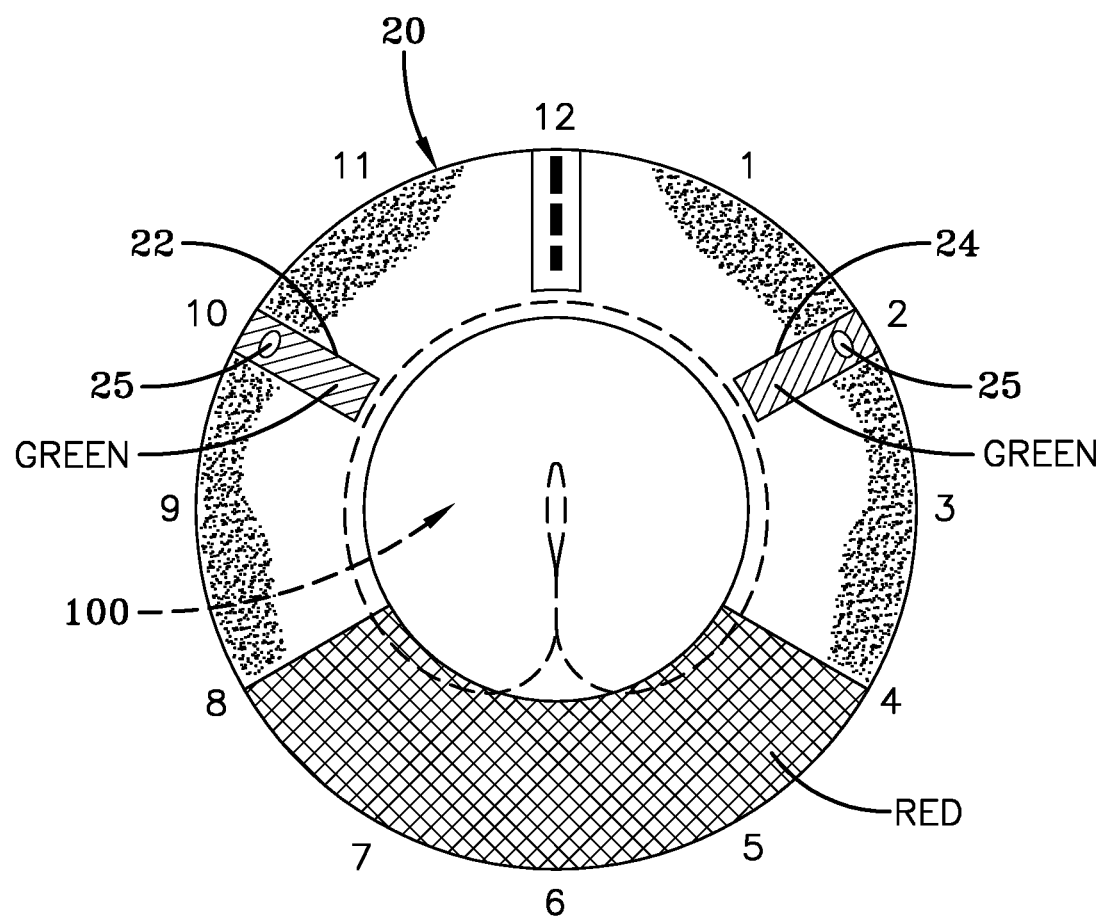
FIG. 4 is an end view of the guide taken from FIG. 1.

As illustrated in FIG. 4, the conformable guide 20 when in an annular shape and spirally wrapped, has a clock-like arrangement indicated as 12 hours. At the 12 hour or top location is a tear strip 30. This tear strip 30 will lie directly on top of the erect penis 100 as shown in FIG. 3 and is provided to facilitate removal of the conformable guide 20 after injection procedures are completed. On either side of the tear strip 30, at preferably the 2 and 10 o'clock positions, are injection guide markers 22, 24, as illustrated these are preferably color coded. In the illustrated embodiment, it is desirous these are illustrated as green indicating the preferred location for which injections should occur. Each green indicator 22, 24 has a plurality of holes or openings 25 extending along the length of the conformable guide 20, as shown in FIG. 3.

Figure 5:
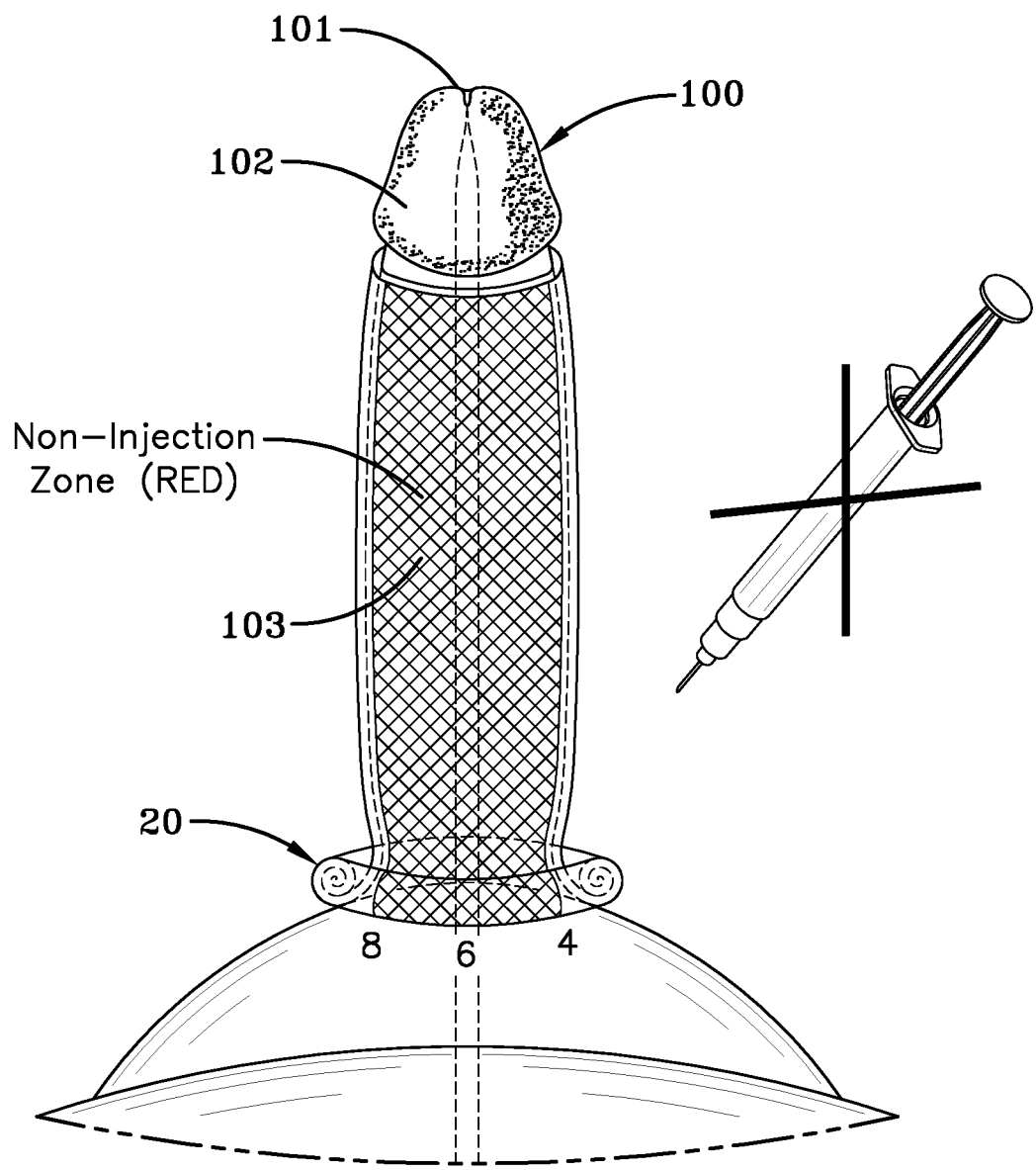
FIG. 5 is a perspective view of the guide taken from FIG. 3 showing the conformable guide from an opposite perspective.

As illustrated in FIG. 5, the 6 o'clock position and extending on either side thereof is a large red colored indicator mark. The red indicator mark is preferably emboldened with the words, "Do not inject here". The location is preferably extended from the 5 to 7 o'clock position more preferably from the 4 to the 8 o'clock position. This red marker lies on the underside of the shaft 103 of the penis 100 and is provided to caution the doctor or patient, if self-injecting, to not inject in this location to avoid the urethra and other danger areas such as neuro-vascular bundles that could cause damage if injected so the person injecting does not hit them with an injection. Additional red zones indication no injections can optionally be indicated at the 11 o'clock and 1 o'clock position on the upper side of the shaft 103. Accordingly, the preferred injection locations are provided at the upper side of the shaft 103 at the indicators 22, 24 as illustrated in FIG. 3.

As shown in FIG. 3, syringes 60 are provide with needles or cannulas 62 to deliver any medicants or stem cells along the shaft 103. As illustrated, the conformable guide 20 is placed on an erect penis 100, it is preferable that the injections be strategically made along the shaft of the penis. Accordingly, the holes 25 are positioned at approximately 3 or 5 mm apart and the injections are made in a series along the indicators 22, 24. The surgeon may at his preference provide the medicants and compositions being delivered along the shaft 103 of the penis 100 anywhere along these openings 25. However, it is believed that a uniform and compartmentalized delivery of such injections is preferred along the entire length of the shaft 103 in most cases.

The conformable guide 20 of the present invention is ideally suited for use in penile treatments as described in WO 2016/127153 A1 which is being incorporated by reference herein and as described below.

Treatment of Peyronie's Disease (PD):

A composition of the present invention is administered to subjects having Peyronie's disease (PD). Peyronie's disease is an ailment involving the growth of fibrous scar tissue, or plaques, in the soft tissue of the penis, which results in abnormal bending of the organ. The etiology of the plaques is not known. These plaques grow in the tunica albuginea, a region of connective tissue that is part of the more general connective tissue of Bucks fascia. The tunica albuginea is an area surrounding the corpora cavernosa. The disease results in pain, erectile dysfunction (ED), and alteration of penis shape, and may be caused by disorganized collagen fibers. Treatments for the disease currently include administration of corticosteroids to the plaques, radiation therapy, and vitamin E. Pharmaceuticals for treatment exist; however, the use of medicaments is considered controversial.

Prior to administration of a composition of the present invention, baseline measurements are taken to assess the state of health of the subjects. These assessments include the following:

Subjects will have peak penile artery velocity in the corporal arteries measured with penile doppler and ultrasound. Penile doppler is a standard tool for the evaluation of ED, and is less invasive than typical means for measuring artery velocity, angiography with selective internal iliac angiography. Penile Doppler may be performed with a high frequency transducer (7.5-9.0 MHz), and at least the inner diameter of the cavernosal artery, baseline peak systolic velocity, and end diastolic velocity are measured. A normal value for inner diameter of the cavernosal artery is 0.3-0.5 mm. In a flaccid state, monophasic flow should be seen in an individual without Peyronie's disease. In an erect state, a velocity of greater than 30 cm/sec should be observed in an individual without ED, which is often a symptom of Peyronie's disease.

In addition to penile artery velocity, the size of fibrous plaques present on the penis is also assessed prior to the initiation of any treatment. This may be done with ultrasound, at which time the grade of Peyronie's may be assigned to the subject. Peyronie's grades are given according to the following: Grade 1 (plaque less than 0.3 cm), Grade 2 (greater than 0.3 cm and less than 1.5 cm), and Grade 3 (greater than 1.5 cm, or two plaques greater than 1 cm).

Angle of penile curvature, a hallmark of Peyronie's disease, is also measured prior to initiation of treatment. Curvature may be assigned a grade according to the following, based on the Kelami classification system: Grade 1

(curvature of 30 degrees or less), Grade 2 (curvature of 30 degrees to 60 degrees), and Grade 3 (curvature of greater than 60 degrees).

A penile rigidity test is also performed prior to initiation of treatment. This test may be done as a nocturnal penile tumescence (NPT test) or an intracavernosal injection test. In an NPT test, the frequency and quality of an erection during sleep is assessed by either placing a ring-like device around the subject's penis, or by use of an electronic monitoring device. The ring-like device is a simple mechanical device consisting of plastic films, which shear at certain pressures, for example when an erection provides sufficient pressure on the ring to break the film. The electronic measurement includes a device that measures frequency, temporal length, and rigidity of erections during sleep. This is a preferred means for measuring rigidity. These variations of the NPT test may be conducted in a polysomnography or other sleep lab, or at the subject's home. The NPT test is usually performed over two consecutive nights for accuracy.

Another form of rigidity test, the intracavernosal injection test, involves injection of alprostodil (a formulation of prostaglandin El available under the trade names EDEX® from Actient Pharmaceuticals and CAVERJECT® from Pfizer) or Tri-Mix (a mixture of Prostaglandin El, Phentolamine, and Papaverine) into the base of the penis, which causes an erection through its vasodilator properties. Following the injection, fullness and length of the erection are measured. The test may be repeated as necessary for increased accuracy. The length and circumference of each subject's penis is also assessed prior to treatment.

Subjects are also given the International Index of Erectile Function (IIEF) Questionnaire prior to initiation of treatment. This questionnaire asks subjects to rate various parameters relating to ED by answering fifteen questions, and assigns point values from zero to five to each answer. A score of 25-30 indicates no ED, and a score of 0-6 indicates severe ED. A continuum of moderate to mild ED exists between a score of 7 and 24. A shortened version of the IIEF, the IIEF-5 may be administered. In this short form, five questions are to be answered, and a score of 22-25 means that the subject does not have ED, and a score of 5-7 means the subject has severe ED. A continuum of moderate to mild ED exists between a score of 7 and 22.

Following baseline measurements of the above variables, a composition including stem cells, preferably penile stem cells, is administered to the subject by implantation in the penis. This implantation is by surgical incision and implantation with a biodegradable scaffold having stem cells present therein, by injection of the composition on an injectable fibrin scaffold, or injection of the stem cells alone, or with an injectable fibrin scaffold. Various groups including other elements such as growth factors, anti-inflammatories, antioxidants, and collagenases are included. Injections are made into the tunica albuginea surrounding the corpora cavernosa and/or the corpora cavernosa themselves, any artery feeding penile tissue, or the corporal arteries or internal pudendal arteries. Repeated injections may be necessary.

Following administration of the composition, follow-up observations, including each of the aforementioned variables (arterial velocity, penile plaque size, penile curvature, IIEF score, and rigidity testing) are collected at three months, six months, and twelve months. Increased velocity, decreased plaque size, decreased curvature, increased IIEF score, and increased rigidity are expected. Shortening of time for improvement is expected in those receiving collagenase as well.

Treatment of Erectile Dysfunction (ED)

A composition of the present invention is administered to subjects having erectile dysfunction (ED). ED is an ailment in which a male is unable to achieve or sustain an erection suitable for sexual intercourse. A number of factors are believed to play a role in or be directly responsible for ED, including obesity, blood pressure, chronic illnesses such as diabetes, poor blood flow to the penis, smoking tobacco, alcoholism, and side-effects of other medications.

Treatments for ED currently include cessation of potential causes such as smoking tobacco and consumption of alcohol, hormone (testosterone) replacement, surgery, and administration of pharmaceuticals such as vardenafil, tadalafil, and sildenafil. Some of these pharmaceuticals are controversial for their incompatibility with nitrate drugs, and for their unwanted side-effects, such as effects on vision (blurring, loss of vision) and priapism.

Prior to administration of a composition of the present invention, baseline measurements are taken to assess the state of health of the subjects. These assessments include the following:

Subjects will have peak penile artery velocity in the corporal arteries measured with penile doppler and ultrasound, as discussed above. In a flaccid state, monophasic flow should be seen. In an erect state, a velocity of greater than 30 cm/sec should be observed in an individual without ED.

A penile rigidity test is also performed prior to any initiation of treatment. This test may be done as a nocturnal penile tumescence (NPT test) or an intracavernosal injection test, as discussed above. Another form of the rigidity test is the intracavernosal injection test, which as discussed above, involves injection of alprostadil (a formulation of prostaglandin E) available under the trade names EDEX® from Actient Pharmaceuticals and CAVERJECT® from Pfizer) or Tri-Mix (a mixture of Prostaglandin El, Phentolamine, and Papaverine) into the base of the penis causing an erection. Following the injection, fullness and length of the erection are measured. The length and circumference of each subject's penis is also assessed prior to treatment.

As discussed above, subjects are also given the International Index of Erectile Function (IIEF) Questionnaire—or shortened version of the IIEF, the IIEF-5—prior to initiation of treatment.

Following baseline measurements of the above variables, a composition including stem cells, preferably penile stem cells, is administered to the subject by implantation in the penis. This implantation is by surgical incision and implantation with a biodegradable scaffold having stem cells present therein, by injection of the composition on an injectable fibrin scaffold, or injection of adipose tissue and stem cell alone. Various groups including other elements such as growth factors, anti-inflammatories, antioxidants, and collagenases are included. Injections are made into the tunica albuginea surrounding the corpora cavernosa and/or the corpora cavernosa themselves, any artery feeding penile tissue, or the corporal arteries or internal pudendal arteries. Repeated injections may be necessary.

Following administration of the composition, follow-up observations, including each of the aforementioned variables (arterial velocity, rigidity testing, and IIEF score) are collected at three months, six months, and twelve months. Increased velocity, increased IIEF score, and increased rigidity are expected.

Examples: Treatment of Peyronie's Disease, Erectile Dysfunction and Other Penile Defects with Penile Stem Cells Patients with erectile dysfunction (ED), Peyronie's Disease (PD) and penile fibrotic trauma were selected. They were given an artificial erection with Tri-Mix (a mixture of Prostaglandin El, Phentolamine, and Papaverine), which allows the corpora cavernosum and the cavernosa spaces to fill and be pressurized with blood. The stem cells are believed to live in the crevices of the corpora.

After applying local anesthesia to each patient, a large bore needle was inserted into the corpora cavernosa and aspirated to obtain 60 cc of blood and blood products. The blood and blood products, were centrifuged (e.g., in a centrifuge used for deriving platelet rich plasma or for separating bone marrow stem cells from the fluid derived from a bone marrow aspiration) to separate the fluid into different cell layers, including a layer of mononuclear cells and platelet rich plasma. The platelet rich plasma layer was extracted and collected, which provided 10 mL of blood product substantially free of red blood cells, which was rich in growth factors and penile stem cells. The mononuclear cell layer was also extracted since it is expected to have penile stem cells.

This fluid containing the penile stem cells had a cell count of ~10<6> mononuclear cells, which is 2-5 times greater than normal plasma. The cells were plated and grown. Stem cells were found to be present in a higher concentration then is found in typical blood. Flow cytometry was performed to further characterize the penile stem cells (See Table 1).

Each patient was given an artificial erection. The fluid containing the penile stem cells was injected back into the erect penis of the patient from which it was derived. Since the patient had an artificial erection the cellular material was able to stay in the penis without the need for a penile clamp to keep the fluid in. If the penis had gone flaccid, a penile ring or clamp could have been used to keep the fluid in.

For the erectile dysfunction patient, the fluid was evenly injected into both corpora cavernosum.

For the Peyronie's Disease patient, the fluid was injected into both corpora and around and in all of the penile plaques and abnormal areas of the tunica albuginea.

For the penile trauma patient and/or patient with Priapism, the fluid is injected it in both corpora and in the fibrotic areas.

The patients were examined at two and three weeks after the procedure. The patients showed much improvement with them getting erections more often. Furthermore, the Peyronie's Disease patient no longer had pain associated with erections; the fibrotic trauma patient had a softer penis.

In a patient with an active priapism, the priapism is drained the same technique of centrifuging and reinjecting the cells is performed.

All of the above treatments described herein are ideally suited with the conformable guide 20.

TABLE 1

| | TNC/mL | CFU-F Frequency | CFU-F per ml | CD34+ % | CD34+ cells/mL | CD146+ % | CD146+ cell/mL |
|---|---|---|---|---|---|---|---|
| 12/22 - Sample 1 | $9.55 \times 10^6$ | 0 | 0 | No data | No data | No data | No data |
| 12/22 - Sample 2 | $11.3 \times 10^6$ | 1/250,000 | 45 | No data | No data | No data | No data |
| 12/22 - Sample 3 | X | X | X | X | X | X | X |
| 2/6 - BM 1 | $20.6 \times 10^6$ | 1/250,000 | 82.6 | 8.09% | $3.06 \times 10^5$ | 1.51% | $31.2 \times 10^4$ |
| 2/6 - Penis PRP 1 | $8.75 \times 10^6$ | 0 | 0 | 6.16% | $5.39 \times 10^5$ | 0.57% | $4.99 \times 10^4$ |
| 2/6 - Penis PRP 2 | $5.56 \times 10^6$ | 0 | 0 | 6.52% | $3.63 \times 10^5$ | 1.05% | $5.84 \times 10^4$ |
| 4/17 - Penis PRP 1 | $36.5 \times 10^6$ | TBD | TBD | X | X | X | X |
| 4/17 - Penis PRP 2 | $18.9 \times 10^6$ | TBD | TBD | X | X | X | X |
| 4/17 - Penis PRP 3 | $10.3 \times 10^6$ | TBD | TBD | X | X | X | X |
| Typical Whole Blood | 800K - 4 million | 0 | 0 | 1 -4% | $10^5$-$10^5$ | Not in literature | Not in literature |
| Typical PRP | 5-20 million | 0 | 0 | 2-7% | $10^5$-$10^5$ | Not in literature | Not in literature |
| Typical BMA | 1-10 million | 1/75,000 | 100-1000/m L | 3-8% | $10^5$-$10^5$ | Not in literature | Not in literature |
| Typical BMC | 20-100 million | 1/50,000 | 1000-5000/mL | 4-12% | $10^6$-$10^7$ | Not in literature | Not in literature |

| Collagenase Digested Biopsy Tissue | | | | | | | |
|---|---|---|---|---|---|---|---|
| | TNC per punch | CFU-F Freq. | CFU-F per punch | CD34+ % | CD34+ cells/mL | CD146+ % | CD146+ cell/mL |
| 2/6 -Tissue Biopsy 4 punches | $6.75 \times 10^4$ | 1/30,000 | 2.3 | Not enough cells | Not enough cells | Not enough cells | Not enough cells |
| 4/17 Patient 1 Tissue | All Punches $2.36 \times 10^5$ | TBD | TBD | Not enough cells | Not enough cells | Not enough cells | Not enough cells |
| 4/17 Patient 3 Tissue | All Punches $2.8 \times 10^5$ | TBD | TBD | Not enough cells | Not enough cells | Not enough cells | Not enough cells |

While the present invention has been described in connection with the preferred embodiments, it is to be understood that other similar embodiments may be used or modifications and additions may be made to the described embodiments for performing the same function of the present invention without deviating therefrom. Therefore, the present invention should not be limited to any single embodiment, but rather construed in breadth and scope in accordance with the recitation of the appended claims.

The conformable guide in addition to being configured for directing injections along the shaft is also ideally suited as an elastic wrap providing a low or moderate level of compression on the shaft. The guide, when used as a wrap, provides an ideal device to secure the shaft after surgery or in the event of a trauma injury. In many penile procedures, an implant of material such as collagen or stem cells laden onto a scaffold or matrix. After such procedure, the wound can be closed using a glue or absorbable sutures and then the shaft is covered in bandages in what is commonly called a mummy wrap. The guide can neatly replace such bandages when placed over the shaft by sealing blood flow, reducing swelling and bruising effects by surrounding the shaft under the compression of the guide. In this situation, the guide can have the injection marker stripes identified by indicating dots or circles to locate injection points rather than holes, as an alternative. In this way, the guide can be completely sealed on the shaft. Accordingly, ointments and topical medicine can be applied onto the shaft and the guide then applied over the coated shaft, thereby keeping the region clean and preventing seepage or staining of underwear and pants of the patient while protecting the incisions or injury from infection. As can be seen, the guide device provides not only a valuable tool for the surgeon but is a great device to prevent post-surgery complications. Furthermore, the easy tear line allows removal of the guide without stressing the wound or incision and as such, the shaft can be exposed as needed to clean blood and apply fresh ointments as needed with replacement guides being applied to insure the shaft is protected from infections during healing. It is believed the guide provides a more reliable way to protect the penis than conventional bandage wraps.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of treating a patient's penis comprises the steps of:
    providing a conformable guide having an elastomeric tube having an open end distally for passing over a glans and a shaft of a penis toward a root of said penis on placement; an annulus shaped wrapped portion of the elastomeric tube at a distal end configured to unwrap on placement toward said root, wherein the elastomeric tube has a longitudinal length and a top side placement indication at a 12 o'clock or 0 degree orientation at a top side of the elastomeric tube with a tear strip extending along the length of the elastomeric tube; and wherein the elastomeric tube has one or more observable color coded injection site locations marked green or otherwise indicated on either side of the tear strip on the elastomeric tube with holes, openings, dots or circles extending along a at least a portion of the length of the elastomeric tube, wherein the injection site locations are at 10 o'clock and 2 o'clock locations relative to the tear strip at 12 o'clock or 0 degree orientation of the top side and wherein the elastomeric tube has a red indicator mark as a no injection marker indication at a location of about 6 o'clock or 180 degrees spanning a width of 5 to 7 o'clock or 135 to 225 degrees relative to the 12 o'clock or 0 degree orientation of the top side extending along the length of the elastomeric tube;
    placing the conformable guide onto the penis;
    aligning the top side placement indication of said guide with a top side of the penis;
    passing the guide over the glans onto the shaft and moving a distal portion of said guide onto the root of said shaft;
    injecting medications through the one or more said injection site locations into said penis to treat the penis; and
    removing the conformable guide after treating the patient by tearing the tear strip along the length of the elastomeric tube.

2. The method of claim 1 wherein said moving the distal portion of said guide onto the root of said shaft further comprises unwrapping the conformable guide.

3. The method of claim 2 wherein the patient is provided a treatment or dosage of material to induce an erection prior to placement or after placement of the conformable guide.

4. The method of claim 1 wherein the method further comprises:
    keeping the conformable guide on the penis after the treatment of the penis as a compression wrap and thereafter removing the conformable guide.

5. The method of claim 1 wherein the method further includes the step of:
    inducing an erection of the penis prior to placing the conformable guide onto the penis.

6. The method of claim 5 wherein the method further includes the step of:
    stretching the conformable guide onto the erect penis as part of the placing the conformable guide onto the penis.

7. The method of claim 6 wherein the method further comprises the step of:
    applying a compressive force around a tissue of the erect penis with the conformable guide.

8. The method of claim 1 wherein the annulus shaped portion which has been unwrapped comprises an annulus shaped portion at the root which holds the elastomeric tube securely to said root of said shaft.

9. The method of claim 1 wherein the elastomeric tube is a synthetic polymer configured in size to stretch when placed over an erect shaft thereby providing a compressive force around tissue of the erect shaft.

* * * * *